(12) United States Patent
Lepsch et al.

(10) Patent No.: US 9,372,182 B2
(45) Date of Patent: Jun. 21, 2016

(54) FUEL COMPOSITION IDENTIFICATION SYSTEM AND METHOD AND FLUID COMPOSITION IDENTIFICATION METHOD

(75) Inventors: Fernando Lepsch, Campinas SP (BR); Tulio Italico Moreira Coletto, Saúde (BR); Fernando de Oliveira Júnior, Campinas SP (BR)

(73) Assignee: Robert Bosch Limitida, Campinas SP (BR)

( * ) Notice: Subject to any disclaimer, the term of this patent is extended or adjusted under 35 U.S.C. 154(b) by 569 days.

(21) Appl. No.: 13/825,594

(22) PCT Filed: Sep. 23, 2011

(86) PCT No.: PCT/BR2011/000342
§ 371 (c)(1),
(2), (4) Date: Aug. 14, 2013

(87) PCT Pub. No.: WO2012/037631
PCT Pub. Date: Mar. 29, 2012

(65) Prior Publication Data
US 2013/0315278 A1 Nov. 28, 2013

(30) Foreign Application Priority Data

Sep. 23, 2010 (BR) ..................................... 1015785

(51) Int. Cl.
*G01N 25/00* (2006.01)
*G01K 17/00* (2006.01)
(Continued)

(52) U.S. Cl.
CPC ................ *G01N 33/22* (2013.01); *G01N 25/08* (2013.01); *G01N 33/2852* (2013.01)

(58) Field of Classification Search
USPC ..................................... 374/45, 141, 144, 32
See application file for complete search history.

(56) References Cited

U.S. PATENT DOCUMENTS

| 5,182,942 A | 2/1993 | Hartel et al. |
| 2003/0056577 A1 | 3/2003 | Ottow et al. |

(Continued)

FOREIGN PATENT DOCUMENTS

| DE | 102006025076 | 12/2007 |
| EP | 1610125 | 12/2005 |

(Continued)

OTHER PUBLICATIONS

International Search Report and Written Opinion for Application No. PCT/BR2011/000342 dated Dec. 7, 2011 (11 pages).

*Primary Examiner* — Mirellys Jagan
(74) *Attorney, Agent, or Firm* — Michael Best & Friedrich LLP (57) ABSTRACT

This invention refers to a fuel composition identification system and method (2) for an automotive vehicle combustion engine. The system comprises at least a fuel heating resistor (3) arranged in any position in the fuel tank or along the fuel line, in direct contact and exchanging heat with the fuel (2), an electronic control unit (4) connected to the resistor (3), which applies constant power values during time intervals (tn) to the resistor (3), and the metering device (6) for a heating resistor parameter (3) between the current sent to the resistor (3) and the surface temperature of the resistor that sends the measured values to the electronic control unit (4), and monitors the current values measured in the heating resistor (3) during each time interval tn, and when the electronic control unit (4) detects a variation in the value of the heating resistor current in the course of the time interval (tn), it identifies the fuel composition corresponding to the critical heat flow resulting from the power applied to the resistor during that time interval. The method comprises the steps of applying constant power values during time intervals (tn) to the fuel heating resistor (3); heating fuel in contact with the heating resistor (3) through exchanging heat between the heating resistor and the fuel (2); measuring a heating resistor parameter (3) between the current sent to the resistor (3) and the surface temperature of the resistor; monitoring the heating resistor parameter values (3) measured in the course of each time interval (tn), and when a variation in the resistor parameter value is detected in the course of the time interval (tn); identifying the fuel composition corresponding to the critical heat flow resulting from the power applied to the resistor during that time interval.

15 Claims, 3 Drawing Sheets

(51) Int. Cl.
  *G01N 33/22*  (2006.01)
  *G01N 25/08*  (2006.01)
  *G01N 33/28*  (2006.01)

(56) References Cited

U.S. PATENT DOCUMENTS

2004/0013912 A1   1/2004   Preidel
2004/0180447 A1   9/2004   Ament et al.
2004/0190587 A1   9/2004   Eisenschmid et al.
2010/0204928 A1   8/2010   Lepsch et al.

FOREIGN PATENT DOCUMENTS

| JP | 2221848 | 9/1990 |
| JP | 1113568 | 1/1999 |
| WO | 2009094735 | 8/2009 |

FUEL COMPOSITION IDENTIFICATION SYSTEM AND METHOD AND FLUID COMPOSITION IDENTIFICATION METHOD

This invention refers to a fuel composition identification system and method used in a flex fuel type automobile, through which identification is made on the basis of the critical heat flow value for each fuel measured during the heating thereof.

DESCRIPTION OF THE STATE OF THE ART

There is a notable worldwide trend towards the adoption of flex fuel type vehicles, in order to lessen the consumption of non-renewable fossil fuels and extend the use of renewable fuels such as ethanol, with less damage to the environment. In this context, it is of interest that the vehicle should be able to identify the composition of the fuel being used at the time, in order to adapt its functioning to the composition characteristics of such fuel.

Some devices and systems are already known in the state of the art that can identify the fuel being used in the vehicle, for example, indicating the proportion of ethanol and/or gasoline in the fuel line. These devices and systems use the assorted physical properties of the fuel or the fuel heating elements to identify the proportions of the mix.

Patent document JP12013568 addresses a device distinguishing the properties of fuel injected into the motor. A fuel detection chamber is fitted close to the injection valve and detects the level of fuel being introduced into a chamber. The fuel is heated in the chamber by a heater fitted outside the chamber. A pressure sensor is fitted inside the chamber. When the fuel reaches a certain level in the chamber, the heater remains switched on until the temperature reaches a predetermined value, with the vapor pressure and the temperature used to identify the fuel properties. In other words, the fuel is identified on the basis of the pressure and temperature thereof.

Patent document JP2221848 also describes a fuel mix ethanol concentration detector whose operations are switched on by injecting a specified quantity of fuel through a syringe into a fuel tank metering cell. The heater is energized and its temperature is measured by a thermistor. The time when the temperature starts to rise is detected by an initial status adjustment section, and the fuel mix is evaporated after the temperature increase starting time. The temperature rises according to the fuel mix composition. The fuel concentration is thus detected on the basis of the following parameters: the time at which the temperature starts to rise, the evaporation time, and the current and voltage of the heating element.

Patent document EP 1620125 describes a process and a device for determining the vaporization characteristics of liquid fuels. This is intended to identify the vaporization characteristics of the fuel driving the motor, in order to avoid flooding with fuel, releasing large quantities of pollutive gases during start-up. It discloses a process through which the variable resistor type heater is placed in the tank, in contact with the fuel for transferring heat through contact. The heater is heated at least until fuel vapor bubbles form on the heater surface. At this time, the temperature is measured around the heater. In order to identify the fuel vaporization characteristics, it is necessary to measure the boiling point, meaning the temperature at which ebullition begins in the boiling region, or the entire fuel boiling curve region. This effect is achieved by the fact that bubble formation is detected locally in the heater, whereby the influence of heat transfer by convection induced by vapor bubbles between the heater and the liquid fuel is detected on the basis of temperature variations. Although heating continues, the temperature in the heater after vapor begins to form initially remains constant, or at least rises more slowly than before vapor formation.

The fuel boiling behavior may thus be characterized through the transition temperature when the first bubbles are formed. The temperature is measured through the heater resistance value, which depends on the temperature. This document does not specifically mention the critical heat flow, nor does it identify the fuel composition through analyzing temperature behavior. Furthermore, this document does not eliminate the problem of differences found in commercial resistors in terms of the values of their resistances as a function of temperature.

Patent document US 2004/0180447 awarded to GM is based on the fractioned distillation system for identifying the fuel composition. The variable resistors are immersed in the tank in a horizontal position and as the fuel evaporates, each resistor is no longer immersed in liquid fuel. When this occurs, the surface temperature of the resistor increases much faster and consequently the current varies to the same proportion. The temperature rated as critical in this invention is that at which the fuel evaporates and the resistor is no longer immersed in liquid. The GM system uses a constant voltage in the resistor in order to calculate the energy consumed. The calculation of the distillation rate is conducted o the basis of the energy consumed in the region with a rapid drop in current.

Patent document DE 20 2006 02576 works through a sensor system fitted in the fuel tank to identify when the tank is filled with the wrong fuel, focused more on distinguishing between gasoline and diesel. To do so, a compartment is fitted in the fuel tank through which the fuel runs when the vehicle is fueled. The heating resistor is placed in the compartment and is powered at a voltage and current to heat the fuel. Identification is conducted essentially on the basis of the boiling point of the fuels, varying significantly between gasoline and diesel. At this time, the transfer of heat from the resistor to the fuel is not longer conductive, instead becoming convective.

This identification may be based on the ebullition time, maintaining the same current, or maintaining the same temperature in the sensor corresponding to an intermediate value between the boiling points of diesel and gasoline, ascertaining when boiling occurs, or through the application of a steadily increasing current, monitoring the behavior of the temperature.

None of the earlier techniques described above uses the critical heat flow parameter to identify the fuel.

Some of the above techniques present the inconvenient aspect of requiring a recipient with a specific fuel volume that is able to measure the parameters required to identify the mix. Earlier techniques on which fuel temperature measurements are based require temperature sensors, which increase the costs of the system and make it more complex. Earlier techniques using variable resistors as a function of temperature and current are subject to low tolerances in resistor fabrication, resulting in inaccuracies in the resistant values measured for each current or temperature value. These parameters vary significantly from one resistor to another.

The critical heat flow concept will be presented in the detailed description of the invention, for an easier understanding of the new concept addressed by this invention.

OBJECTIVES OF THE INVENTION

A first objective of the invention is to provide a system and method for the accurate identification of fuel composition, without the use of recipients with pre-determined volumes, that may be installed anywhere along the fuel lines of vehicles using cold start systems for flex fuel engines already in place on the market.

A second objective of the invention is to provide a system and method for identifying fuel composition that can also detect fuel adulterated with solvents or water.

An additional objective of the invention is to provide a system and method for identifying the composition of a fuel through the power supplied, being immune to functional variations that are common to variable resistors arising from low fabrication tolerance and not requiring the use of temperature sensors.

Another objective of the invention is to provide a system and method for identifying fuel composition which heats the fuel over briefer periods and with less outlays of energy, identifying the optimum heating temperature for each fuel composition.

BRIEF DESCRIPTION OF THE INVENTION

The objectives of the invention are achieved through a system that identifies the composition of the fuel for an automotive vehicle combustion engine, with this system comprising:

at least a fuel heating resistor arranged in any position in the fuel tank or along the fuel line, in direct contact and exchanging heat exchange with the fuel;

an electronic control unit connected to the resistor, which sends a controlled power feed to the resistor;

a metering device that measures the heating resistor parameter between the current sent to the resistor and the surface temperature of the resistor, forwarding the measured values to the electronic control unit, with the electronic control unit applying constant power values to the resistor during preset time intervals ($t_n$), and monitors the heating resistor parameter values measured by the metering device during each time interval $t_n$, and when the electronic control unit detects a variation in the value of the heating resistor parameter in the course of the time interval $t_n$, it identifies the fuel composition corresponding to the critical heat flow resulting from the power applied to the resistor during that time interval, with identification conducted through the following formula:

$$q''\max = \frac{W}{m^2}$$

where:
q"max=maximum critical heat flow
W=maximum critical power applied to the resistor at the instant $t_n$
$m^2$=surface area of the resistor in contact with the fuel.

The measurement device may be a meter measuring the current sent to the resistor, with the heating resistor having a variable resistance value as a function of its temperature. The metering device may also be a temperature sensor that measures the surface temperature of the resistor.

Preferably, the value of the power applied by the electronic control unit to the resistor increases for each successive time interval $t_n$ according to the following formula: $W(t_{n+1})=W(t_n)+X$, where X is the incremental value of the power added at each time interval.

The electronic control unit may comprise a memory containing the critical power values corresponding to each fuel composition as well as the mixes thereof.

The electronic control unit preferably maintains the power applied to the resistor at a constant value equal to that corresponding to the critical heat flow at the time the fuel composition is identified.

The electronic control unit may identify that the fuel is adulterated when the power corresponding to the critical heat flow of the fuel is less than the power corresponding to the critical heat flow of gasoline fuel with minimum ethanol content, or is higher than the power corresponding to the critical heat flow of fuel containing only ethanol.

Preferably, at least one fuel heating resistor is fitted in the fuel injection pipe.

Alternatively, the electronic control unit applies the initial power value to the resistor which is higher than the critical power of the maximum ethanol fuel content, and reduces the power at each successive time interval $t_n$, according to the following formula:

$W(t_n)+1)=W(t_n)-X$, where X is the decreasing value of the power, stepped down at each time interval, with the electronic control unit identifying the fuel composition when it detects that the resistor heating parameter value remains constant during the time interval $t_n$.

The objectives of the invention are also achieved through a fuel composition identification method for an automotive vehicle combustion engine, comprising the following steps:

Apply the controlled power value to the fuel heating resistor, which is in contact with the fuel, fitted in the fuel or along the fuel line, heating fuel in contact with the heating resistor and through exchanging heat between the heating resistor and the fuel, and measuring a heating resistor parameter between the current sent to the resistor and the surface temperature of the resistor, with constant power values applied to the resistor at the fuel heating step during pre-set time intervals $t_n$, with this method also comprising the following steps:

monitoring the heating resistor parameter values measured in the course of each time interval $t_n$; and when a variation occurs in the resistor parameter value in the course of the time interval $t_n$, and this is detected, identifying the fuel composition corresponding to the critical heat flow resulting from power applied to the resistor during that time interval, identified through the following formula:

$$q''\max = \frac{W}{m^2}$$

where:
q"max=maximum critical heat flow
W=maximum critical power applied to the resistor
$m^2$=surface area of the resistor in contact with the fuel Preferably, the value of the power applied to the resistor is increased at each successive time interval $t_n$ according to the following formula: $W(t_{n+1})=W(t_n)+X$, where X is the incremental value of the power added at each time interval.

The step of identifying the fuel composition may include consulting a pre-programmed memory containing the critical power values corresponding to each fuel composition as well as the mixes thereof.

Preferably, after the fuel composition identification step, the power applied to the resistor is kept at a constant value equal to that corresponding to the critical heat flow at the time when the fuel composition if identified.

Alternatively, the initial value of the power applied to this resistor is higher than the critical value of fuel with maximum ethanol content, with the power stepped down at each successive time interval $t_n$ according to the following formula: $W(t_n)+1)=W(t_n)-X$, in which X is the decreasing value of the power stepped down at each time interval and the fuel composition is identified when the value of the heating resistor parameter in the course of the time interval $t_n$ remains constant.

Finally, the objectives of the invention are achieved through a fluid composition identification method comprising the following steps:

Applying the controlled value of the power to the heating resistor, which is in contact with the fluid in the tank, heating the fluid in contact with the heating resistor through a heat exchange between the heating resistor and the fluid, and measuring a heating resistor parameter between the current sent to the resistor and the surface temperature of the resistor, with constant power values applied to the resistor during time preset intervals $t_n$ during the fluid heating step; and The method also comprises the following steps of monitoring the heating resistor parameter values measured in the course of each time interval $t_n$, and when a variation occurs in the resistor parameter value in the course of the time interval $t_n$, and this is detected, identifying the composition of the fluid corresponding to the maximum critical heat flow resulting from the power applied to the resistor during that time interval, with identification through the following formula:

$$q''\max = \frac{W}{m^2}$$

q"max=maximum critical heat flow
W=maximum critical power applied to the resistor
$m^2$=surface area of the resistor in contact with the fuel.

BRIEF DESCRIPTION OF THE DRAWINGS

This invention will be described in greater detail below, based on a specific example presented in the drawings. The figures show.

DETAILED DESCRIPTION OF THE FIGURES

The system and method for identifying fuel composition in flex fuel type automotive vehicles, pursuant to this invention, are based on the critical heat flow concept. When heated to boiling point, fluids run through various heating phases, from natural heat convection to heating with bubbles, through to the formation of a film between the hot surface and the fluid.

Figure 5:
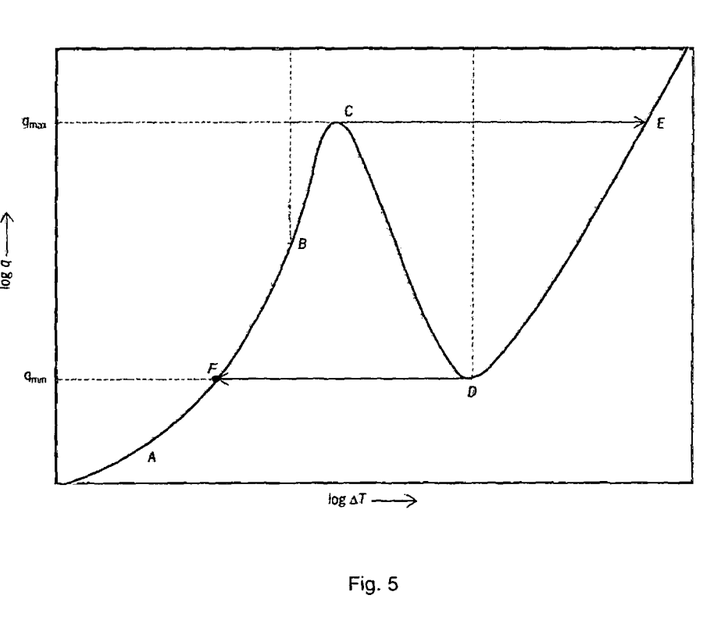
FIG. 5 is a liquid boiling curve showing relation between the heat flow from the heater to the liquid and the temperature variation.

These phases are illustrated in the graph presented in FIG. 5, in terms of the flow of heat from the heater to the liquid. This in principle is applied to fuel burned by combustion engines, which is heated by resistors called heat injectors, or heating plugs, or simply heaters. When heating occurs, the liquid fuel is located in the same environment as the heating resistors, coming into direct contact with them and resulting in transfers of heat between the resistor surface and the fuel.

At the time when the heat transfer reaches a specific value, a vapor film starts to form between the hot surface of the heating resistor and the liquid fuel, when the temperature rises sharply on the resistor surface. The point at which this phenomenon occurs at the start of the vapor film formation corresponds to what is known as the maximum critical heat flow, identified as Point C in the graph presented in FIG. 5, which is the maximum critical point of the heat flow graph. At this time, the heat flow from the resistor to the liquid undergoes an alteration in behavior resulting in a variation in the temperature of the resistor. The critical heat flow may be calculated as shown in the following formula:

$$q''\max = 0.149 * hfg * \rho v [\sigma * g * (\rho l - \rho v)/\rho v^2]^{1/4} \qquad \text{(Formula I)}$$

Where:
q"Max Maximum critical heat flow=$W/m^2$
hfg Latent vaporization heat
$\rho v$ Vapor density
$\rho l$ Liquid density
$\sigma$ Surface tension
g Gravity As the resistor continues to heat up, the heat flow shifts from Point C to Point E, as shown in the graph presented in FIG. 5, indicated by the arrow linking these two Points.

Another critical heat flow point in the liquid boiling graph is the minimum heat flow, corresponding to Point D in the graph presented in FIG. 5. This minimum heat flow value is normally attained when the liquid is overheated and goes through a cooling process, through which the temperature gradually drops, as though the graph were following the reverse path, from right to left.

Point D corresponds to the moment when the heater surface of the heating resistor, for example, is completely covered by vapor bubbles. When the heating resistor temperature values are higher than Point D and are lowered by power sent to the resistor, the heat flow drops steadily (as shown in the graph, in the interval between the Point and Point D). From Point D onwards, if the power sent to the resistor continues to drop, the heat flow shifts in the graph presented in FIG. 5 from Point D directly to Point F, as shown by the arrow linking these two points, without including the maximum heat flow value corresponding to Point C. So, as the power is reduced, the heat flow drops and the surface temperature of the resistor also falls sharply, until reaching Point F, which is the minimum heat flow point.

The critical heat flow points depend on some specific physical properties of the heated substance, such as latent vaporization heat, surface tension and density. Consequently, this concept is applied to this invention, leading to the conclusion that the critical heat flow point values are different and specific for each type of fuel composition, depending on their properties. In this case, this critical heat flow will thus vary as a function of the proportion between ethanol and gasoline, or possibly the presence of solvents or water in the fuel mix.

The heat flow is expressed in the unit $W/m^2$. This means that at the maximum (C) and minimum (D) critical points, W is the maximum or minimum "critical power" supplied to the heating resistor, divided by the "area" of the heating resistor that dissipates the heat. This area corresponds to the surface of the heating resistor in contact with the fuel being heated. Considering that the heating resistor has a contact surface equivalent to a heat transfer area in m², with value, the maximum and minimum critical power values will thus determine the type of fuel. Thus, as fuel composition varies with the amount of ethanol blended with gasoline, the critical power value corresponding to the critical heat flow points will consequently also vary as a function of the proportion of ethanol in the fuel mix, as illustrated in the graph presented in FIG. 1. The higher the ethanol content in the mix, the higher the maximum and minimum critical power values.

As is generally known, the gasoline currently sold on the Brazilian market always has specific ethanol content. Gasoline with lower ethanol content is called E22, with 22% ethanol in its composition. In the graph presented in FIG. 1, the lowest critical power value corresponds to fuel consisting of pure gasoline, which is used in some countries. However, this invention may be used when considering the lowest critical power for gasoline with a lower ethanol content (E22). The highest critical power value shown in FIG. 1 corresponds to a fuel consisting of pure ethanol. Thus, the intermediate values correspond to the different mix proportions. The lower the ethanol content in the fuel, the lower the minimum critical power found by the system addressed by this invention.

Figure 2:
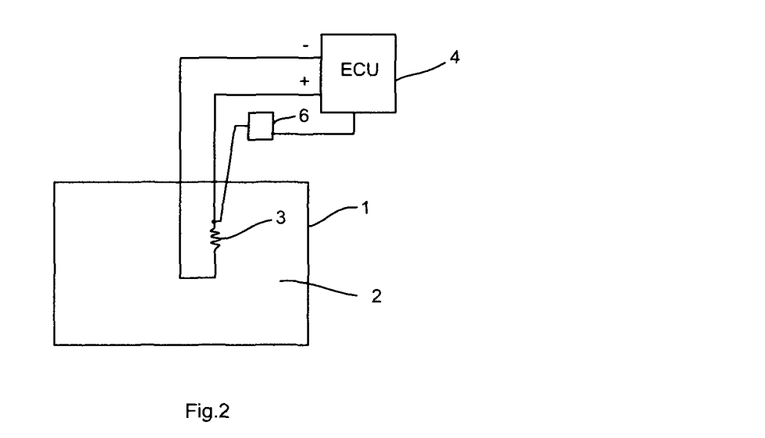
FIG. 2 is a schematic overview of the fuel identification system according to a type of the invention.

FIG. 2 a schematic overview of the fuel identification system arrayed in compliance with a mode of this invention, which is applied to a flex fuel type combustion engine in an automotive vehicle. The system comprises at least the fuel heating resistor 3 which may be placed in any position along the route of the fuel, in the fuel tank or along fuel line 1, being in direct contact and exchanging heat with the fuel 2. For the preferred mode of the invention, heating resistor 3 is fitted in the fuel injection pipe. There is no need to place it in a recipient with a known fuel volume, as the evaporated fuel volume or the evaporation time does not interfere with the functioning of the system.

The system comprises an electronic control unit 4 connected to the resistor 3, which applies a controlled power heat to the resistor 3, heating it and dissipating heat into the fuel.

Furthermore, the system presents a metering device 6 for a heating resistor 3 parameter, which is monitored and used as a basis for identifying that the system has reached maximum or minimum critical power, corresponding to the maximum or minimum critical heat flow of the fuel being used. The values measured by the heating resistor parameter are forwarded to the electronic control unit 4 that monitors possible variations in this parameter.

The resistor parameter that may be monitored, indicating the maximum or minimum critical power are the current (or resistance or voltage) of the resistor and the resistor temperature. As the value of the power applied to the resistor is constant at each time interval $t_n$, the values of the current sent to the resistor and the resistor temperature also remain constant during this same time interval $t_n$, when the power applied is less than the maximum critical power. However, both parameters alter abruptly when the maximum critical power is attained. Thus, the key grounds underpinning the system addressed by this invention consist of detecting this variation in the resistor parameter being monitored, identifying the power applied to the resistor at that time as being the maximum critical power for that fuel composition, and consequently identifying the corresponding fuel composition.

When the parameter monitored is the current sent to the resistor 3, the metering device used by the system is the current meter. In this case, the use of temperature sensors is avoided, as the heating resistor must be the resistor with a variable resistance value as a function of its temperature, with PTC or NTC characteristics. This is because when reaching the maximum critical heat flow, a fuel vapor film forms around the heating resistor, insulating the resistor from the liquid phase of the fuel, resulting in rapid heating and consequently altering its resistance. As the power applied by the electronic control unit to the resistor is constant at each time interval $t_n$, an alteration in the resistance of the heating resistor 3 during this interval will result in the current sent to it, also altering it rapidly. This variation in the measurement of the current sent to the resistor will indicate that the maximum critical power has been attained.

When the monitored parameter is the surface temperature of the resistor 3, the metering device used by the system is the temperature sensor of the resistor. When the fuel vapor film forms around the heating resistor, insulating the resistor from the liquid phase of the fuel, the resistor then exchanges heat with vapor instead of liquid. This shift in the fuel phase also causes an alteration in the heat transfer coefficient and consequently alters the surface temperature of the resistor. In this case, a heating resistor with a fixed resistance value may be used, as well as a resistor with PTC or NTC characteristics. Thus, in this mode of the invention, the temperature variation measured at the resistor will indicate that the maximum critical power was attached.

Figure 3:
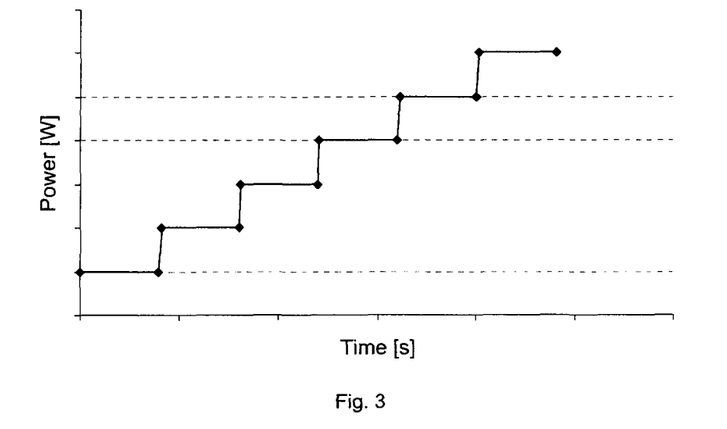
FIG. 3 is a graph showing the power application step at levels to the heating resistor used in the fuel identification method addressed by this invention.

When the fuel is being heated, the electronic control unit 4 applies constant power values to the resistor during identical pres-set time intervals $t_n$. In a preferred mode of the invention, the value of the power applied is stepped up steadily for each successive time interval $t_n$ as illustrated in the graph presented in FIG. 3.

Figure 1:
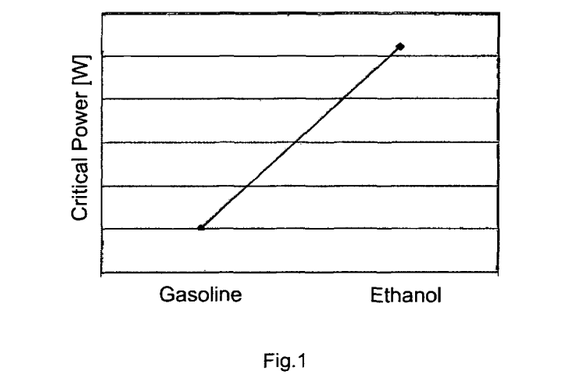
FIG. 1 is a graph illustrating the variation in the critical power as a function of the proportion of ethanol and gasoline in the fuel mix.

The lowest initial power value must be less than the maximum critical power value for fuel containing only gasoline, as shown in FIG. 1. Should fuel not be present, when applying the initial power, the current and temperature measurements of the resistor present variations, and the system identifies that the sensor is not immersed in fuel, aborting the fuel detection step and switching off the heater. The highest power value that the system can apply must necessarily be higher than the critical power of fuel containing only ethanol, also shown in FIG. 1.

The initial power applied must be less than the minimum critical power corresponding to pure gasoline or with minimum ethanol content. For each time interval, the power is preferably stepped up by the same incremental value X, as shown in the following formula: $W(t_n)+1)=W(t_n)+X$.

The intermediate levels of power between the maximum pure ethanol and minimum pure gasoline values correspond to the intermediate blends of gasoline and ethanol. The incremental value X is determined at the design phase as a function of the accuracy required for identifying the fuel. The higher the value of X, the lower the accuracy of the system. However, if lower X values are used, the system may be extremely accurate for identifying fuel.

The values of the temperature or the current sent to the resistor are steadily fed into the electronic control unit 4 monitoring variations in these values during the time interval $t_n$. When the current or temperature values remain constant during the same interval, this means that the maximum critical power of the fuel in question has not yet been reached, so the electronic control unit then steps up the power by X during the subsequent interval. This increase in the power levels naturally triggers an increase in the proportion levels of the temperature and the current measured at the resistor, although the increased value remain constant during the subsequent step. This behavior is illustrated in the graph presented in FIG. 4 showing the variation in the levels of power applied to the resistor and the proportional variation of the resistor current corresponding to an increase in the power during the first three time intervals.

Figure 4:
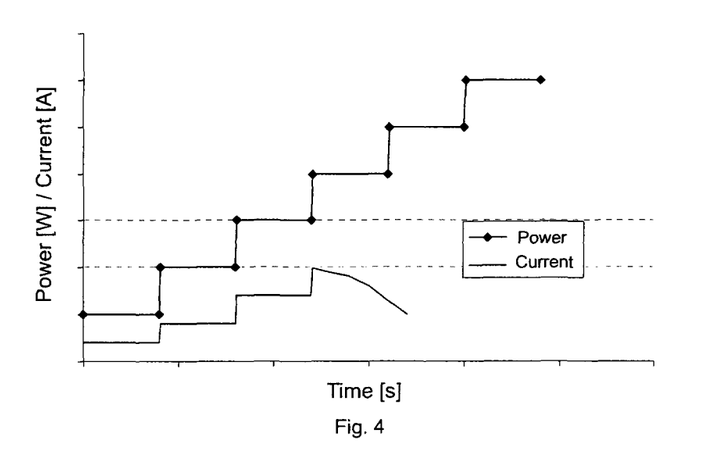
FIG. 4 is a graph showing the power variation at levels applied to the heating resistor and the variation in the measured current sent to the resistor in compliance with the fuel identification method and system addressed by the invention.

Thus, as shown in FIG. 4, when electronic control unit 4 detects a variation in the value of the heating resistor current during the course of time interval $t_n$, (in this case n=4), it identifies that the value power applied at that time is the maximum critical power value for that fuel composition. This critical power is calculated on the basis of the following critical heat flow formula:

$$q''\max = \frac{W}{m^2} \qquad \text{(Formula II)}$$

where:
q"max=maximum critical heat flow
W=power applied to the resistor
$m^2$=surface area of the resistor in contact with the fuel.

Bringing this formula II to the same level as formula I present above, leads to the conclusion that the maximum critical power, which is directly proportional to the maximum critical heat flow is also specific to each type of fuel. Thus, as the surface of the resistor in contact with the fuel ($m^2$) is fixed and determined at the design the electronic control unit is thus able to identify the fuel composition as a function of the maximum critical power W applied to the resistor during that time interval.

Preferably, the electronic control unit (4) has a memory that stores the maximum and/or minimum critical power values for each fuel composition, as well as those of their blends. These values are calculated previously based on Formulas I and II presented here and registered in the database that is accessed by the electronic control unit when it identifies that the critical power value has been reached. At this time, the electronic control unit 4 continues to send power to the resistor noting the value of the maximum critical power corresponding to the moment at which the fuel composition if identified, or a value slightly higher than this critical power.

This is because the main objectives of the invention are to heat the fuel more quickly and with less energy outlays, identifying the fuel composition through discovering the optimum heating temperature for each fuel composition. It is advantageous for the system to operate by heating the fuel in a temperature range just below the formation temperature of this steam film. When the film forms, the resistor begins to exchange heat with the vapor, which is an exchange more difficult than with liquid fuel, with less energy efficiency, so the optimum heating temperature is just below the film formation temperature, which is the highest possible heating temperature with the fuel still in a liquid state. Thus, the fastest heating rate is achieved with the greatest possible energy efficiency. As the critical heat flow is directly proportional to the power applied to the resistor and inversely proportional to the surface area of the resistor in contact with the fuel (Formula II, then the parameter for the surface area of the resistor in contact with the fuel may also be adjusted during the design step, in order to adapt the system addressed by the invention to the constraints imposed by cold start-up system in automotive vehicles already in place on the market. As is known, these systems may impose constraints in terms of the maximum voltage and power values that may be applied to the resistor. Thus, the value of the surface area of the resistor in contact with the fuel is determined in advance, in order to allow the system to operate within the entire critical power bracket for all possible compositions of gasoline and ethanol, even within the voltage and power constraints imposed by existing start-up systems, not requiring any other adaptations to hardware or software.

The system addressed by this invention may also be used to identify whether fuel has been adulterated. When gasoline is adulterated with solvents, the properties of the solvent lower the maximum critical heat flow value, meaning that the maximum critical power will be less than the minimum critical power shown in the graph presented in FIG. 1, corresponding to gasoline with minimum ethanol content.

When ethanol is adulterated with water, its maximum critical heat flow value increases, whereby the maximum critical power found will be higher than the maximum critical power corresponding to pure ethanol. Thus, the electronic control unit identifies that the fuel is adulterated when the power corresponding to the maximum critical heat flow of the fuel is less than the power corresponding to the maximum critical heat flow of fuel containing only gasoline, or is higher than the power corresponding to the maximum critical heat flow of fuel containing only ethanol.

This invention also addresses a fuel composition identification method for an automotive vehicle combustion engine. This method essentially comprises the steps already mentioned here, although described in greater detail below, as they must be construed on the basis of the concepts presented here for the critical heat flow points and their application for identifying the fuel composition in due fuel type vehicles.

The first step of the method consists of applying a controlled power value to the fuel heating resistor 3, which is direct contact with the fuel 2, fitted in the fuel tank or along the fuel line of the vehicle, preferably in the fuel injection pipe. The fuel is then heated by contact with heating resistor 3 through exchanging heat between the heating resistor and the fuel 2. At this fuel heating step, constant power values are applied to the resistor 3 during identical pre-set time intervals $t_n$ during the heating step, and at each time interval $t_n$, the heating resistor 3 parameter is measured, which may be the current sent to the resistor 3 or the surface temperature of the resistor. This measurement step, when it consists of metering the current, is handled through a resistor current meter. When measuring the surface temperature of the resistor, this step is handled through a temperature sensor.

The measured resistor parameter values (related to either current or temperature) are monitored during each time interval $t_n$ and must remain constant in each interval, as the power applied is also constant. When a variation in the resistor parameter value is detected during the time interval $t_n$, the method then moves into the step of identifying the fuel composition. This step is handled in the following manner:

The value of the power applied to the resistor at that moment in time is considered as the maximum critical power for that fuel composition, which corresponds to the maximum critical heat flow of this composition, according to the following formula:

$$q''\max = \frac{W}{m^2} \qquad \text{(Formula II)}$$

where:
q"max=maximum critical heat flow
W=maximum critical power applied to the resistor
$m^2$=surface area of the resistor in contact with the fuel It is thus sufficient to find the fuel composition corresponding to the critical power value found.

The value of the power applied to the resistor is preferably increased for each successive time interval $t_n$ according to the following formula $W(t_{n+1})=W(t_n)+X$, where X is the incremental value of the power added at each time interval. These successive increases in power continue until the maximum critical power is attained, meaning that the power applied to the resistor is maintained at a value equal to that corresponding to the maximum critical heat flow at the time of identification of the fuel composition, or slightly above the critical power.

The step of identifying the fuel composition is preferably conducted by consulting a pre-programmed memory that contains the maximum critical power values corresponding to each fuel composition, as well as for the blends thereof. These values are calculated in advance with the assistance of Formulas I and II, stored in this database.

The system and the method addressed by this invention may also use this application of power values at constant values during each time interval $t_n$, although starting with a power value higher than the highest critical power value corresponding to the fuel with the highest ethanol content (generally, pure ethanol, and progressively stepped down by this power until reaching the value of the minimum critical power corresponding to the minimum critical heat flow (Point D in FIG. 5). Thus, for each successive time interval $t_n$, the power applied is stepped down in compliance with the following formula: $W(t_{n+1})=W(t_n)-X$, in which X is the value decreasing value of the power at each time interval. These successive reductions in power continue until the minimum critical power is reached, on which occasion constant behavior with no variation in current or temperature is observed for the resisfor being monitored. This occurs when the power applied to the resistor is higher than the critical power identified as Point D in FIG. 5, with temperature and the current varying significantly during the same time interval $t_n$. When the power reaches the minimum critical value of Point D or even lower values, less than the value corresponding to the minimum critical heat flow of Points D and F, the temperature and current remain constant during the interval $t_n$. It is recalled that this phenomenon occurs when the power is stepped down steadily and the heat flow follows the path of the graph presented in FIG. 5 from Point E to Point D, and then directly to Point F without passing through Point C. This power bracket that is less than the minimum critical power correspond to the power and temperature values prior to those at Point D or F in the graph presented in FIG. 5, and, during this phase, the current and temperature values for the resistor surface remain constant for a constant power value. When the method and system identify that the resistor current power or the temperature of this resistor remain constant, this means that the current power sent to the resistor is already lower than the maximum critical power. Thus, for this mode of the invention, the critical power used as a basis for identifying the fuel composition will be that applied to the resistor during the previous time interval $t_{(n-1)}$, which will be equal to $W(t_n)+X$.

It is thus noted that the identification of the fuel composition is conducted solely on the basis of identifying the behavior of the variation in the current or the surface temperature of the resistor, with no need for accurate measurements of any type of electrical or physical parameter in the circuit or the fuel in order to identify the fuel composition. The only parameter that must be metered is the power applied to the resistor, with this power applied by the control unit, consequently not subject to significant measurements errors The identification is the fuel composition based only on variations in current or temperature makes the system and the method addressed by this invention immune to metering inaccuracies arising from the limitations in the resolutions of the devices used or even defects in such devices, as well as very frequent variations in the physical and electrical characteristics of the devices arising from low fabrication tolerances. The method addressed by this invention may be used for identifying the composition of fluids other than fuel blends, applied to flex fuel type engines.

This method of identifying the composition of fluids is conducted in the following manner.

The controlled power value is applied to the heating resistor, which is in contact with the fluid to be identified, with the fluid being stored in a recipient. The power is applied to the resistor at constant values during identical pre-set time intervals ($t_n$). The fluid in contact with the heating resistor is heated through exchanges of heat between the heating resistor and the fluid, as it is energized. While the fluid is being heated by the resistor, the heating resistor parameter is measured, which may be the current sent to the resistor or the surface temperature of the resistor during time intervals ($t_n$).

By monitoring the heating resistor parameter values measured during each time interval $_n$, and when a variation is detected in the resistor parameter value during a time interval, the composition of the fluid is identified, corresponding to the maximum critical heat flow resulting from the power applied to the resistor during that time interval. This identification is handled through the following formula:

$$q''\max = \frac{W}{m^2}$$

where:

q"max=maximum critical heat flow

W=maximum critical power applied to the resistor $m^2$=surface area of the resistor in contact with the fuel.

Having described an example of the preferred realization of this invention, it must be understood that the scope of this invention comprises other possible variations, being limited only by the content of the appended claims, including possible equivalents thereof.

The invention claimed is:

1. A fuel composition identification system for an automotive vehicle combustion engine, the system comprising:

a fuel heating resistor placed in a position in the fuel tank or along the fuel line, in direct contact and exchanging heat with the fuel;

an electronic control unit connected to the resistor which applies a controlled feed power to the resistor;

a metering device which measures a parameter of the heating resistor, the parameter being the current on the resistor or the surface temperature of the resistor, and sends the metered values to the electronic control unit, wherein the electronic control unit applies constant power values to the resistor during pre-set time intervals and monitors the heating resistor parameter values measured by the metering device during each time interval ($t_n$), wherein when the electronic control unit detects a variation in the heating resistor parameter value during the time interval ($t_n$), it identifies the fuel composition corresponding to the maximum critical heat flow resulting from the power applied to the resistor during that time interval, the identification being conducted through the following formula:

$$q''\max = \frac{W}{m^2}$$

wherein:
q"max=maximum critical heat flow
W=maximum critical power applied to the resistor at time ($t_n$)
$m^2$=surface area of the resistor in contact with the fuel.

2. The fuel composition identification system according to claim 1, wherein the measurement device is a current meter that measures the current on the resistor, wherein the heating resistor has a resistance value variable as a function of its temperature.

3. The fuel composition identification system according to claim 1, wherein the metering device is a temperature sensor that measures the temperature on the surface of the resistor.

4. The fuel composition identification system according to claim 1, wherein the value of the power applied by the electronic control unit to the resistor is stepped up at each successive time interval ($t_n$) according to the following formula: $W(t_n+1)=W(t_n)+X$, wherein X is the incremental value of power added at each time interval.

5. The fuel composition identification system according to claim 1, wherein the electronic control unit comprises a memory containing the maximum critical power values corresponding to each fuel composition as well as blends thereof.

6. The fuel composition identification system according to claim 1, wherein the electronic control unit maintains the power applied to the resistor at a constant value equal to that corresponding to the maximum critical heat flow at the time of the identification of the fuel composition.

7. The fuel composition identification system according to claim 1, wherein the electronic control unit identifies that the fuel is adulterated when the power corresponding to the critical heat flow for the fuel is less than the power corresponding to the critical heat flow of fuel containing only gasoline or is higher than the power corresponding to the critical heat flow of fuel containing only ethanol.

8. The fuel composition identification system according to claim 1, wherein at least a fuel heating resistor is placed in the fuel rail.

9. The fuel composition identification system according to claim 1, wherein the electronic control unit applies an initial power value to the resistor which is higher than the maximum critical power of fuel with a maximum ethanol content and steps down the power at each successive time interval $t_n$, according to the following formula: $W(t_n+1)=W(t_n)-X$, in which X is the decreasing power value stepped down for each time interval, with the electronic control unit identifying the fuel composition, when it detects that the heating resistor parameter value remains constant in the course of the time interval ($t_n$).

10. A fuel composition identification method for an automotive vehicle combustion engine, the method comprising:
applying a controlled power value to the fuel heating resistor that is in contact with the fuel inside the fuel tank or along the fuel line;
heating fuel in contact with the heating resistor by exchanging heat between the heating resistor and the fuel; and
measuring a heating resistor parameter, the parameter being the current on the resistor and the surface temperature of the resistor,
wherein, during the fuel heating step, constant power values are applied to the resistor during pre-set time intervals ($t_n$),
the method also comprising the steps of:
monitoring the heating resistor parameter values measured in the course of each time interval $t_n$, and
when a variation in the resistor parameter value occurs in the course of the time interval $t_n$, and this variation is detected, identifying the fuel composition corresponding to the maximum critical heat flow resulting from the power applied to the resistor during that time interval, this identification being conducted through the following formula:

$$q''\max = \frac{W}{m^2}$$

wherein
q"max=maximum critical heat flow
W=maximum critical power applied to the resistor
$m^2$=surface area of the resistor in contact with the fuel.

11. The fuel composition identification method according to claim 10, wherein the value of the power applied to the resistor is stepped up at each successive time interval ($t_n$) according to the following formula: $W(t_{n+1})=W(t_n)+X$, in which X is the incremental power value added at each time interval.

12. The fuel composition identification method according to claim 10, wherein the fuel composition identification step includes consulting a pre-programmed memory containing the maximum critical power values corresponding to each fuel composition, as well as blends thereof.

13. The fuel composition identification method according to claim 10, wherein after the fuel composition identification step, the power applied to the resistor is maintained at a constant value equal to that corresponding to the maximum critical heat flow at the time of identifying the fuel composition.

14. The fuel composition identification method according to claim 10, wherein the initial value of the power applied to the resistor (3) is higher than the maximum critical power of the fuel having maximum ethanol content and the power is stepped down at each successive time interval ($t_n$) according to the following formula: $W(t_{n+1})=W(t_n)-X$, wherein X is the decreasing value of the power stepped down at each time interval and the fuel composition is identified when the heating resistor parameter value remains constant during the time interval ($t_n$).

15. A fluid composition identification method comprising the following steps:
applying a controlled power value to a heating resistor which is in contact with the fluid in a recipient;
heating the fluid in contact with the heating resistor by exchanging heat between the heating resistor and the fluid; and
measuring a heating resistor parameter, the parameter being the current on the resistor and the surface temperature of the resistor;
wherein at the fluid heating step, constant power values are applied to the resistor during pre-set time intervals ($t_n$); and the method further comprising the steps of:
monitoring the heating resistor parameter values measured in the course of each time interval ($t_n$), and
when a variation in the resistor parameter value occurs in the course of the time interval ($t_n$), and this variation is detected, identifying the composition of the fluid corresponding to the maximum critical heat flow resulting from the power applied to the resistor during that time interval, the identification being conducted through the following formula:

$$q''\max = \frac{W}{m^2}$$

wherein:
q"max = maximum critical heat flow
W = maximum critical power applied to the resistor
$m^2$ = surface area of the resistor in contact with the fuel.

* * * * *